US00PP34848P2

(12) United States Plant Patent
Clark

(10) Patent No.: US PP34,848 P2
(45) Date of Patent: Dec. 13, 2022

(54) ***COLEUS* PLANT NAMED 'UF18-51-6'**

(50) Latin Name: *Coleus scutellarioides*
Varietal Denomination: UF18-51-6

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/803,410

(22) Filed: Jun. 24, 2022

(51) Int. Cl.
*A01H 6/00* (2018.01)
*A01H 5/12* (2018.01)

(52) U.S. Cl.
USPC ..... Plt./469

(58) Field of Classification Search
USPC ..... Plt./469
CPC ..... A01H 6/00; A01H 5/12
See application file for complete search history.

(56) References Cited

U.S. PATENT DOCUMENTS

PP28,517 P2 10/2017 Clark et al.

*Primary Examiner* — Keith O. Robinson
(74) *Attorney, Agent, or Firm* — Katherine Koenig; Koenig IP Works, PLLC

(57) ABSTRACT

A new and distinct cultivar of *Coleus* (*Coleus scutellarioides*) plant named 'UF18-51-6', selected for having a combination of desirable traits that make it well-suited for good performance as an annual plant in the summer landscape. 'UF18-51-6' has large leaves that are predominantly deep purple, with contrasting pink centers, and well-defined yellow green leaf margins. 'UF18-51-6' maintains these colors in a broad range of environmental conditions, and it has received superior ratings in both sun and shade trials. It is upright and compact in habit, but it is highly branched and uniform in shape, and grows wider than it does tall. This allows the plant to have high utility for use in any part of the garden landscape.

3 Drawing Sheets

Genus and species: *Coleus scutellarioides*.
Cultivar denomination: 'UF18-51-6'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF18-51-6'. The new cultivar 'UF18-51-6' originated from an open pollination conducted in May-November 2017 in Citra, Fla. between the female *Coleus* plant 'UF16-26-10' (unpatented) and an unknown male *Coleus* plant. A single seedling was chosen in May 2018 for further asexual propagation in Gainesville, Fla.

The new cultivar 'UF18-51-6' has been reproduced asexually for over 18 months through meristem tip cuttings and has been found to retain its distinctive characteristics through successive asexual propagations. 'UF18-51-6' was first propagated asexually by meristem tip cuttings in May 2018 in Gainesville, Fla., and has remained true-to-type since that time.

Plant Breeder's Rights for the new cultivar 'UF18-51-6' have not been applied for, and 'UF18-51-6' has not been made publicly available more than one year prior to the filing date of this application.

When compared to the female parent 'UF16-26-10', the new cultivar 'UF18-51-6' has large leaves that are almost as wide as they are long. Leaves are predominantly deep purple, with yellow green margins and deep pink center. In contrast, the female parent 'UF16-26-10' has smaller leaves that are twice as long as they are wide, and the leaves are colored dark maroon with dark green margins and have only a trace of pink color on older leaves. 'UF18-51-6' has a vigorous upright and compact habit that is well-branched, whereas 'UF16-26-10' is less vigorous, and more spreading in habit with less lateral branching.

The new cultivar 'UF18-51-6' was selected for its consistent foliage color patterning, and also for its fast growth rate and vigor in the greenhouse and landscape. Historically, pink foliage color in *Coleus* was often linked to weak growth and burning of foliage in full sun. 'UF18-51-6' has foliage that is predominantly deep purple with consistent pink centers, and bright lime green accents at the leaf margin. Normally this color combination fades in either full sun (all maroon-brown) or full shade (all green), with the consistent loss of pink color. 'UF18-51-6' is exceptional because it maintains a strong pink center and bright yellow green margins in a broad range of environmental conditions. It is a vigorous genotype that can easily grow four feet tall in the landscape, maintaining similar color in both sun and shade. Vegetative cuttings from 'UF18-51-6' form roots in one week and consistently produce vivid pink center color in the greenhouse, making it a visually appealing plant for mass markets.

SUMMARY OF THE INVENTION

The new cultivar 'UF18-51-6' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF18-51-6' when grown under normal horticultural practices in Gainesville, Fla. 'UF18-51-6' has the combination of vigorous, upright and compact growth habit, excellent heat tolerance, and consistent multicolored leaves that are significantly different than other *Coleus* plants. It has superior stability in foliage color in both sun and shade conditions, maintaining stable color in all conditions. It has excellent lateral branching, making it suitable for propagators and producers. 'UF18-51-6' has been observed to have long-season performance in landscape trials in Gainesville, Fla.

DESCRIPTION OF THE FIGURES

This new *Coleus* culver 'UF18-51-6' is illustrated by the accompanying photographs, which show the plant's form and foliage. The colors shown are as true as can be reasonably obtained by conventional photographic procedures.

FIG. 2 shows the growth habit, form, and foliage of the claimed plant; and

FIG. 3 shows a close-up view of the foliage of the claimed plant

DETAILED BOTANICAL DESCRIPTION OF THE CULTIVAR

Figure 1:
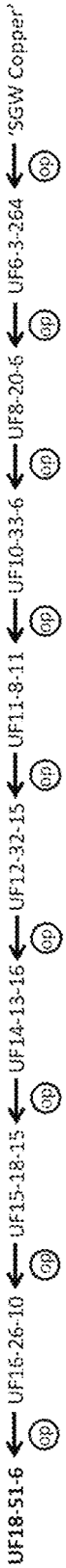
FIG. 1 shows the pedigree of the claimed plant.
Figure 2:
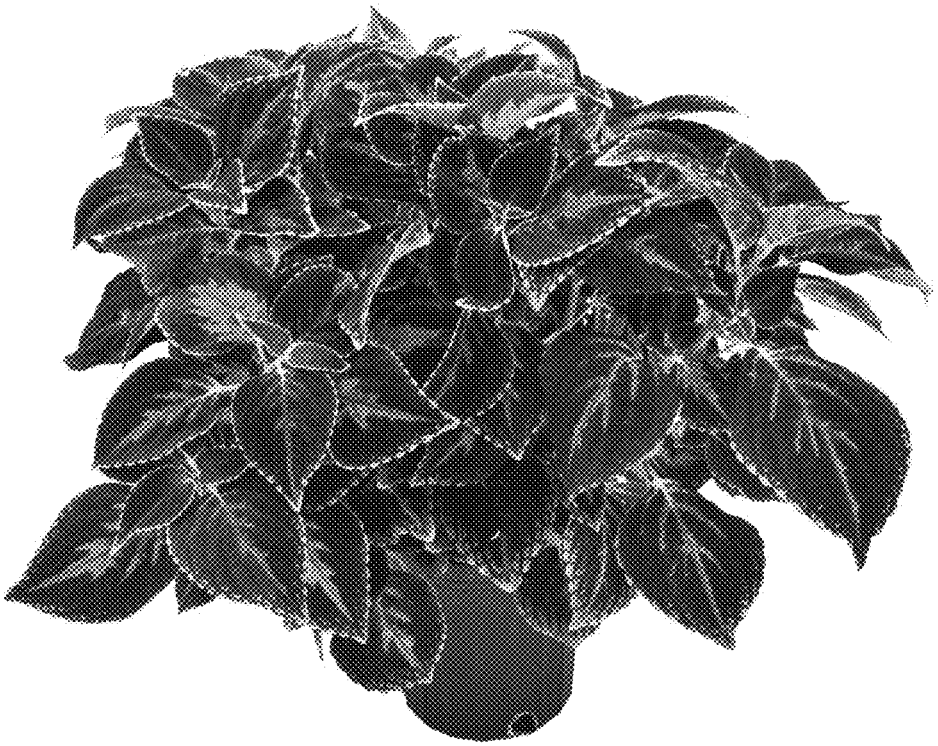
FIGS. 2 and 3 were taken from plants grown nine weeks from unrooted cuttings in September-November 2021 in a glass-covered greenhouse in Gainesville, Fla.
Figure 3:
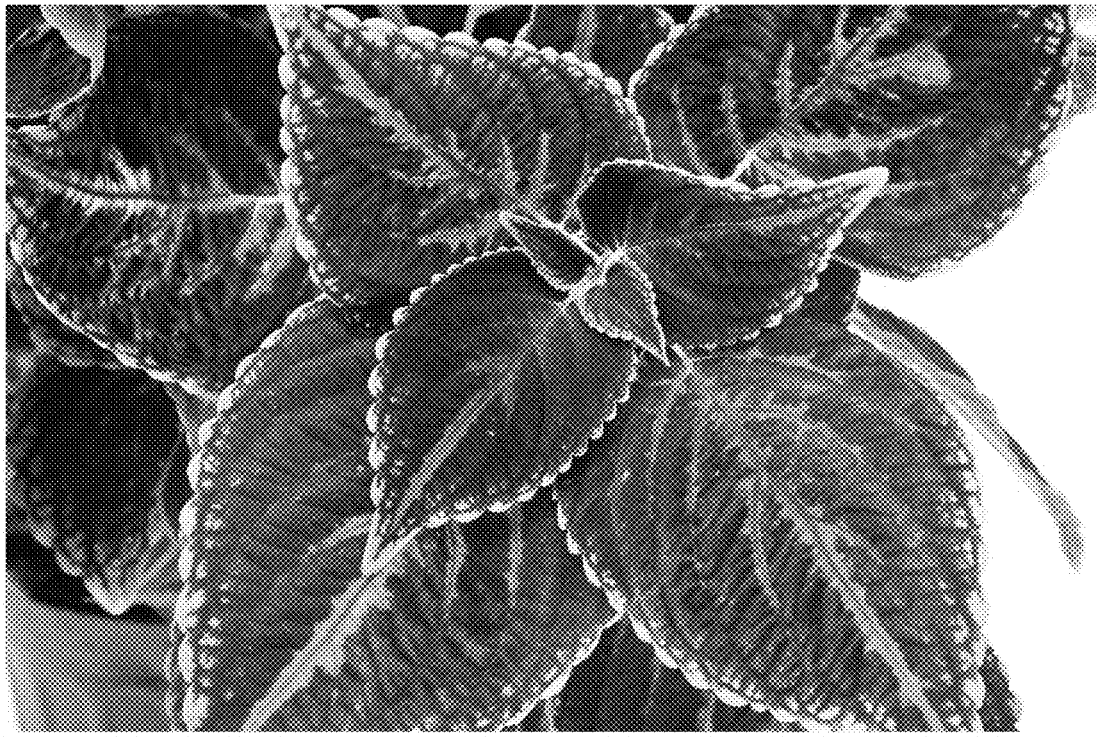

Foliage color was determined using The R.H.S. Colour Chart of The Royal Horticultural Society of London (R.H.S.), 2007 ($5^{th}$ Edition) under full sun conditions in the middle of the day in a glass-covered greenhouse. *Coleus* leaves are rarely one solid color but encompass hues, shades and tints, and color patterns differ from one genotype to another due to varying levels of variegation.

DESCRIPTION OF GROWING CONDITIONS

The detailed description below was generated using nine-week-old plants of the new cultivar 'UF18-51-6' (from the time the cutting was harvested and stuck) pinched once at four weeks after stick and grown in a poly-covered greenhouse in September-November 2021 in Gainesville, Fla.

BOTANICAL DESCRIPTION

Botanical classification:

*Family*.—Lamiaceae.

*Botanical name*.—*Coleus scutellarioides*.

*Common name*.—*Coleus*.

*Cultivar*.—'UF18-51-6'.

Parentage:

*Female or seed parent*.—'UF16-26-10'.

*Male or pollen parent*.—Unknown.

Plant description:

*Growth habit*.—Upright and compact.

*Plant height* (*from top of soil*).—30-35 cm.

*Plant width* (*horizontal plant diameter*).—55-50 cm.

Propagation:

*Type cuttings*.—Vegetative meristem tip cuttings having at least 1 node.

*Time to initiate roots*.—3-4 days.

*Time to produce a rooted cutting*.—7-10 days.

Roots:

*Rooting habit*.—Fibrous.

*Root description*.—Callus forms in 2-3 days, roots initiate in 3-4 days and become a highly branched cutting in 7-10 days.

Branches:

*Quantity per plant*.—6.

*Branch color*.—RHS 143C (strong yellow green).

*Texture*.—Smooth.

*Pubescence*.—Not present.

*Stem description*.—Square-shaped stem, 1.0 cm in diameter at the soil line.

*Branch diameter*.—0.6-0.8 cm at the base of a 28 cm long branch.

*Branch length*.—28-30 cm.

*Internode length*.—4.0-4.5 cm.

*Anthocyanin*.—Not present.

Foliage description:

*Quantity of leaves per branch*.—18.

*Arrangement*.—Opposite.

*Fragrance*.—Not fragrant.

*Shape*.—Ovate.

*Length*.—11-12 cm.

*Width*.—10-11 cm.

*Apex*.—Broadly acuminate.

*Base*.—Attenuate.

*Margin*.—Lobed.

*Leaf texture* (*both surfaces*).—Smooth.

*Pubescence*.—Not present.

*Venation color*.—Upper surface, proximal (base): RHS N186C (dark greyish red). Upper surface, distal (tip): RHS 145C (light yellow green). Lower surface: RHS 145C (light yellow green).

*Venation pattern*.—Upper surface: Reticulate. Lower surface: Reticulate.

*Color, immature leaf*.—Upper surface, base: RHS 166A (greyish brown). Upper surface, center: RHS 181B (moderate red). Upper surface, margin: RHS 143A (strong yellow green). Lower surface, base: RHS 143A (strong yellow green). Lower surface, center: RHS 196A (greyish yellow green). Lower surface, margin: RHS N186A (dark purplish grey).

*Color, mature leaf*.—Upper surface, base: RHS N186A (dark purplish grey). Upper surface, center: RHS 186B (moderate purplish red). Upper surface, margin: RHS 143A (strong yellow green). Lower surface, base: RHS 146A (moderate olive green). Lower surface, center: RHS 145C (light yellow green). Lower surface, margin: RHS N186D (dark purplish red).

*Petiole length*.—4-5 cm. Petiole diameter: 0.3-0.4 cm. Petiole color: RHS 143C (strong yellow green). Petiole texture: Smooth, no pubescence.

Flowers and seeds: Flowers and seeds have not been observed.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*). This pathogen has been observed in stock materials grown closely together in cooler growing seasons.

COMPARISON WITH KNOWN CULTIVARS

Plants of the new *Coleus* cultivar 'UF18-51-6' can be compared to those of 'UF13-48-27' (sold commercially under the trade name FRENCH QUARTER™, U.S. Plant Pat. No. 28,517). The base color on the upper surface of mature leaves of 'UF18-51-6' is RHS N186A (dark purplish grey), the center color is RHS 186B (moderate purplish red), and the margin color is RHS 143A (strong yellow green). In contrast, the base color on the upper surface of mature leaves of 'UF13-48-27' is RHS 2D (yellowish green), the center color is RHS 60D (purplish red) with RHS N186C (purplish pink) and the margin color is RHS N144A (yellowish green). Additionally, 'UF18-51-6' has thicker stems (1.0 cm in diameter), whereas 'UF13-48-27' has thinner stems (0.6 cm in diameter).

What is claimed is:

1. A new and distinct *Coleus scutellarioides* plant named 'UF18-51-6' as shown and described herein.

* * * * *